United States Patent [19]

Umbach et al.

[11] 3,969,417

[45] July 13, 1976

[54] PROCESS FOR THE ALKOXYLATION OF COMPOUNDS CONTAINING ALCOHOLIC HYDROXYL GROUPS

[75] Inventors: Wilfried Umbach, Langenfeld; Werner Stein, Erkrath-Unterbach, both of Germany

[73] Assignee: Henkel & Cie G.m.b.H., Dusseldorf-Holthausen, Germany

[22] Filed: Apr. 3, 1975

[21] Appl. No.: 564,811

Related U.S. Application Data

[63] Continuation of Ser. No. 293,425, Sept. 29, 1972, abandoned, which is a continuation-in-part of Ser. No. 859,581, Sept. 19, 1969, abandoned, which is a continuation-in-part of Ser. No. 683,446, Nov. 16, 1967, abandoned.

[30] Foreign Application Priority Data

May 16, 1967  Germany............................ 6274212
Nov. 8, 1968  Germany............................ 1807780

[52] U.S. Cl. .......................... 260/615 B; 260/615 R; 260/611 B; 260/613 B
[51] Int. Cl.² .................... C07C 41/02; C07C 41/10
[58] Field of Search ........................ 260/615 B, 615

[56] References Cited

UNITED STATES PATENTS

| | | | |
|---|---|---|---|
| 2,870,220 | 1/1959 | Carter ............................ | 260/615 B |
| 3,219,631 | 11/1965 | Kullman et al. .............. | 260/615 BU |
| 3,393,219 | 7/1968 | Myerly et al. ................ | 260/615 B X |
| 3,425,999 | 2/1969 | Axelrood et al. ............... | 260/615 B |

FOREIGN PATENTS OR APPLICATIONS

| | | | |
|---|---|---|---|
| 898,269 | 11/1945 | France ............................ | 260/615 B |
| 1,557,407 | 1/1969 | France ............................ | 260/615 B |
| 1,807,780 | 9/1970 | Germany......................... | 260/615 B |
| 1,193,924 | 6/1970 | United Kingdom ............. | 260/615 B |
| 796,508 | 6/1938 | United Kingdom ............. | 260/615 B |

OTHER PUBLICATIONS

Merrall et al., Can. J. Chem. 38, pp. 1917–1975, 1960.
Latrimouille et al., J.A.C.S. 82, 120–124, 1960.
Rosenberg et al., J. Polymer Sci., Part C, No. 16, 1917–1929, 1967.
USPB 717, Jan. 11, 1946, 1–10, 14, 17.
USPB 22713–S, Oct. 3, 1947, pp. 1–6, 80–90, 92.

*Primary Examiner*—Howard T. Mars
*Attorney, Agent, or Firm*—Hammond & Littell

[57] ABSTRACT

This invention relates to an improvement in the process of alkoxylation of compounds containing alcoholic hydroxyl groups by reacting compounds containing hydroxyl groups with alkylene oxides in the presence of alkoxylation catalysts. The said improvement involves the use of a tertiary oxonium salt with a substantially non-polarizable halogeno-complex anion as the said alkoxylation catalyst. Use of such catalysts gives lower amounts of unreacted alcohols in the products, particularly when secondary alkanols of 8 to 24 carbon atoms are employed.

16 Claims, No Drawings

PROCESS FOR THE ALKOXYLATION OF COMPOUNDS CONTAINING ALCOHOLIC HYDROXYL GROUPS

PRIOR APPLICATION

This application is a continuation of Ser. No. 293,425, filed Sept. 29, 1972, now abandoned, which in turn is a continuation-in-part of our copending U.S. application Ser. No. 859,581, filed Sept. 19, 1969, now abandoned which in turn is a continuation-in-part of U.S. application Ser. No. 683,446, filed Nov. 16, 1967, and now abandoned.

THE PRIOR ART

The alkoxylation methods, generally used until now, are based on the reaction of the alkoxylatable compounds with alkylene oxides in the presence of alkaline catalysts, such as sodium hydroxide, sodium methylate, sodium ethylate or metallic sodium, at elevated temperatures and increased pressure. In the case of the alkoxylation of compounds containing alcoholic hydroxyl groups, difficulties are encountered during this method of working, since the alcoholic hydroxyl groups of the starting compound exhibit a lower reactivity in relation to the alkylene oxides than the hydroxyl groups of the ether alcohols formed. In other words, when using 1 mol of alkylene oxide to each hydroxyl group of the alcohol, the pure mono-adduct is not obtained, but in addition to appreciable amounts of unreacted starting alcohols, corresponding higher alkylene oxide adducts are obtained.

Thus, the essential purpose of the reaction to obtain the most complete reaction possible, is not fulfilled. On the other hand, the alkoxylated compounds frequently show an undesirable broad spectrum of oxyalkylene homologs. The indicated difficulties, which are noticeable already during the alkoxylation of primary alcohols, occur in increased measure during the alkoxylation of secondary alcohols. The reactivity of a tertiary hydroxyl group relative to epoxides is so slight in the presence of alkaline catalysts, that an alkoxylation can hardly be attained.

By utilizing acid catalysts in the reaction, the reactivity of the original alcoholic hydroxyl groups becomes slightly improved in relation to alkylene oxide. However, such catalysts have not proved successful in the field of the art. They do allow the work to be conducted at lower temperatures, but at the same time, they promote the formation of undesirable by-products, for example, dioxane or dioxolane during the ethoxylation process. These by-products may constitute 10 to 20% of the reacted ethylene oxide. Moreover, acid catalysts have been found questionable with respect to their corrosivity.

According to another suggestion, the alkoxylation is carried out in a two-stage working method. In the first stage, as much as 4 mols of ethylene oxide were reacted with the alcohol in the presence of an acid catalyst. The the reaction mixture was neutralized, the unreacted alcohol was removed, and the ether and polyether alcohol were alkoxylated in the presence of an alkaline catalyst. However, it was not possible by means of this method, to obtain a satisfactory reaction of the alcohol used in the first stage of the process. Beyond that, this multi-stage process, in particular, the necessary separation of the primary product of the first stage, does not offer any satisfactory solution to the problem.

OBJECTS OF THE INVENTION

An object of the invention is to find a process for alkoxylation of aliphatic alcohols having 8 to 24 carbon atoms which
a. can be conducted in one single step, and
b. assures a high degree of reaction of the alcohol used with the alkylene oxide and thus guarantees a narrow spectrum of oxyalkylene homologs in the end product.

Another object of the invention is the development of, in the process of alkoxylation of compounds containing hydroxyl groups by reacting aliphatic alcohols having 8 to 24 carbon atoms with epoxides of the formula

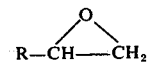

wherein R is a member selected from the group consisting of hydrogen, alkyl having 1 to 2 carbon atoms, hydroxyalkyl having 1 to 2 carbon atoms and haloalkyl having 1 to 2 carbon atoms in the presence of an alkoxylation catalyst, the improvement which comprises using a tertiary oxonium salt with a substantially non-polarizable halogeno-complex anion as said alkoxylation catalyst.

These and other objects of the invention will become more apparent as the description thereof proceeds.

DESCRIPTION OF THE INVENTION

According to the invention, these objects have been achieved in that tertiary oxonium salts with a substantially non-polarizable halogeno-complex anion are employed as catalysts for the alkoxylation process.

These tertiary oxonium salts are compounds derived from aliphatic or cyclic ethers and compounds containing carbonyl groups of the general formulas

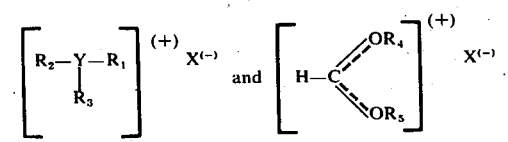

wherein
Y represents an oxygen atom or a C=O group;
X represents an unpolarizable or only slightly polarizable halogeno-complex anion, for example, $BF_4^-$, $FeCl_4^-$, $AlCl_4^-$, $SbCl_6^-$, $SnCl_6^{2-}$;
$R_1$ represents a lower aliphatic radical having from 1 to 4 carbon atoms, or phenyl;
$R_2$ and $R_3$ are alkyl radicals containing from 1 to 24 carbon atoms, aromatic, alicyclic or heterocyclic ring systems having from 3 to 14 ring atoms;
$R_2$ and $R_3$ can also be combined into one ring having from 4 to 14 ring atoms;
$R_4$ and $R_5$ are alkyl radicals containing from 1 to 24 carbon atoms, aromatic, alicyclic or heterocyclic ring systems having from 5 to 20 ring atoms.

The alkyl radicals described can be saturated or unsaturated, straight or branched, substituted, interrupted by hetero atoms, for example, halogen, ether groups or by cyclic groups, or bonded on Y through hetero atoms. The alicyclic or heterocyclic ring systems can be saturated or unsaturated. In the case that $R_2$ and $R_3$ are combined into one ring, this ring can, if so desired, contain hetero atoms and it can also be saturated or unsaturated. All of the ring systems mentioned can contain substituents.

Among the preferred tertiary oxonium salts are compounds of the formula selected from the group consisting of

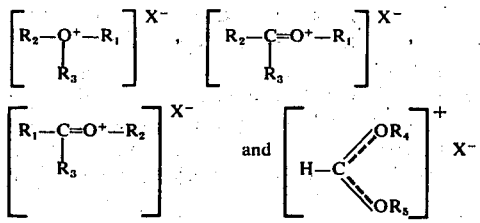

wherein
X represents a halogen-complex anion selected from the group consisting of $BF_4^-$, $FeCl_4^-$, $AlCl_4^-$, $SbCl_6^-$ and $SnCl_6^=$;
$R_1$ represents a member selected from the group consisting of alkyl having from 1 to 4 carbon atoms, alkoxy having from 1 to 4 carbon atoms, haloalkyl having from 1 to 4 carbon atoms and phenyl;
$R_2$ and $R_3$ are members selected from the group consisting of alkyl having 1 to 24 carbon atoms, alkoxy having 1 to 4 carbon atoms, haloalkyl having 1 to 4 carbon atoms, phenyl, phenylvinyl and, when taken together, alkylene having 3 to 14 carbon atoms, oxaalkylene having 2 to 13 carbon atoms, thiaalkylene having 2 to 13 carbon atoms, azaalkylene having 2 to 13 carbon atoms, alkenylene having 3 to 14 carbon atoms, alkadienylene having 4 to 14 carbon atoms and benzobutadienylene;
$R_4$ and $R_5$ are members selected from the group consisting of alkyl having 1 to 24 carbon atoms, haloalkyl having 1 to 8 carbon atoms, phenylalkyl having from 7 to 10 carbon atoms, alkoxyalkyl having from 2 to 24 carbon atoms and cycloalkylalkyl having from 6 to 10 carbon atoms.

Among the tertiary oxonium salts used in the process of the invention, the following can be mentioned as examples:
trimethyloxonium fluoborate
triethyloxonium fluoborate
triethyloxonium hexachloroantimonate
1-ethyl-1-oxa-cyclopentanium hexachloroantimonate
tributyloxonium hexachloroantimonate
1-(4-chlorobutyl)-1-oxa-cyclopentanium hexachloroantimonate
trimethyloxonium tetrachloroferrate
trimethyloxonium tetrachloroaluminate
triethyloxonium tetrachloroaluminate
bis-(trimethyloxonium)-hexachlorostannate
triphenyloxonium fluoborate
O-ethylcamphoroxonium fluoborate
2-ethoxy-1-oxa-cyclopent-1enium fluoborate
O-ethyldibenzalacetonium tetrachloroaluminate
triethylcarbonate-acidium fluoborate
2-ethoxy-1-thiacyclopent-1-enium fluoborate
1-methyl-2-ethoxy-1-aza-cyclopent-1-enium fluoborate
2,3-benzo-6-ethoxypyrylium fluoborate
2-methyl-1,3-dioxolenium fluoborate
2-phenyl-1,3-dioxolenium hexachloroantimonate
2-ethoxy-1-oxa-cyclotridec-1-enium fluoborate.

Of particular advantage is the employment of tertiary oxonium salts wherein Y of the above formula represents the C=O group, and wherein $R_1$, $R_2$, $R_3$ and X have the previous meaning, for example:
O-ethylcamphoroxonium fluoborate
2-ethoxy-1-oxa-cyclopent-1enium fluoborate
O-ethyl-dibenzalacetonium tetrachloroaluminate
and the like.

In addition, compounds of the formula

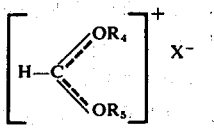

wherein $R_4$ and $R_5$ are alkyl residues containing 1 to 5 carbon atoms are particularly advantageous oxyalkylation catalysts, for example, dimethoxycarbonium tetrafluoroborate, diethoxycarbonium tetrafluoroborate, methoxyethoxycarbonium tetrafluoroborate, dibutoxycarbonium hexachloroantimonate, di-isopentyloxycarbonium hexachloroantimonate. (The nomenclature used does not describe the oxonium character of the compounds evident from the above formula, but is customary in the literature [see "Angewandte Chemie", 1966, 78, p. 714]. For a description of the oxonium structure, the catalysts might be called "dialkylformate-acidium salts" according to the suggestion in Houben-Weyl "Methoden der Organischen Chemie", Vol. 6/3, p. 330.)

The preparation of the tertiary oxonium salts can be carried out according to methods known from the literature (see Houben-Weyl, "Methoden for Organischen Chemie", Vol. 6/3, 4th Edition).

Saturated tertiary oxonium salts, wherein Y of the above formula represents an oxygen atom, are obtained, for example, by the action of metallic and non-metallic halide etherates on epoxides; by the addition of alkyl halides to metallic and non-metallic halide etherates; by alkylation of ethers with halogen alkyls and silver tetrafluoborate; as well as by the effect of aliphatic diazo compounds on primary and secondary oxonium salts. The unsaturated tertiary oxonium salts, wherein Y of the above formula represents a C=O group, are essentially prepared by alkylation of carbonyl compounds with trialkyl oxonium salts or alkyl halide/silver tetrafluoborate mixtures and by action of borontrifluoride or antimony pentachloride on acetals and ortho acid esters. The tertiary oxonium salts designated as carbonium salts are essentially prepared by reacting corresponding orthoformic acid esters with metallic and non-metallic halides which are capable of forming non-polarizable or only slightly polarizable halogen-complex anions, for example, $BF_3$, $AlCl_3$, $FeCl_3$, $SbCl_5$ or $SnCl_4$.

The oxonium salts utilized as catalysts according to the invention may be utilized singly or in admixture with other tertiary oxonium salts. They are usually added to the alcohol to be alkoxylated at amounts of 0.05 to 5%, preferably of 0.1 to 1.5% by weight, based on the amount of the alcohol used.

The process of alkoxylation according to the invention can be employed for all substances containing hydroxyl groups including those in which the acidity of the original hydroxyl group is less than the acidity of the ether and polyether alcohols resulting from the reaction.

Accordingly, mono- and polyhydric alcohols of the aliphatic, cycloaliphatic and alkylaromatic series having from 1 to 24 carbon atoms can be employed as starting substance containing hydroxyl groups. These alcohols can be saturated or unsaturated, straight or branched; their alkyl chains or their ring can be substituted or interrupted by hetero atoms. The hydroxyl group to be alkoxylated can have a primary, secondary or tertiary character. However, and unexpectedly, when aliphatic alcohols having 8 to 24 carbon atoms are employed, particularly secondary alcohols, higher yields of the desired alkoxylated products are obtained as compared with conventional alkoxylation catalysts. Examples of the preferred alcohols are, for example, alkanols having from 8 to 24 carbon atoms, such as n-octanol-1, n-dodecanol-1, n-tetradecanol-1, docosyl alcohol, 2,2,4-trimethylhexanol-6, n-octanol-2, secondary n-tetradecanols, n-pentadecanol-8, 2,5,10-trimethylundecanol-7, and mixtures, etc.; haloalkanols having from 8 to 24 carbon atoms; alkenols and alkadienols having from 4 to 24 carbon atoms, such as oleyl alcohol, linoleyl alcohol, etc.

Moreover, alcohol mixtures, primarily of alkanols having 8 to 24 carbon atoms, can be utilized, for example, fatty alcohol mixtures containing from 8 to 24 carbon atoms, as they are obtained by hydrogenation of the fatty acid mixtures obtained on saponfication of natural fats and waxes according to well known methods, also mixtures of synthetic alkanols which are prepared from petroleum products according to the Ziegler or Oxo process. Moreover, mixtures of predominantly secondary alkanols can be utilized, which are prepared by air-oxidation of straight-chain paraffins in the presence of boric acid or boric acid anhydride, as well as mixtures which contain primary or secondary alkanols together.

All of the substances containing epoxide groups are suitable to serve as alkylene oxides. Of special interest are those epoxide compounds of the formula

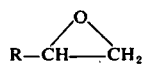

wherein R is a member selected from the group consisting of hydrogen, alkyl having 1 to 2 carbon atoms, hydroxyalkyl having 1 to 2 carbon atoms and haloalkyl having 1 to 2 carbon atoms, for example, ethylene oxide, propylene oxide, butylene oxide, glycide, epichlorohydrin and epibromohydrin.

These epoxides can be added singly or admixed with one another to the alcohol. They can also be added successively in any order chosen at random.

The amount of the alkylene oxide to be added is likewise chosen at random. For various purposes of utilization such amounts of epoxide can be added, that water-soluble products result therefrom. In this case, the amount of the alkylene oxide to be added is to be adjusted to the carbon number of the alcohol as is well known.

In the case where the products to be prepared are to be rendered water soluble by, for example, a sulfating process, the number of the alkylene oxide molecules can be correspondingly smaller.

The process of alkoxylation according to the invention can be effected in the usual manner after an addition of the tertiary oxonium salt to the alcohol to be reacted.

The temperatures employed in this process range between 0° and 200°C., preferably between 40° and 160°C. When unsaturated oxonium salts are used as catalysts, the progress of the reaction shows already at room temperature a high degree of reaction. The possibility of working at favorably low temperatures is of a particular advantageous effect with respect to the quality of the end product, since high temperatures, as it is well known in the art, affect the color of the products obtained and, furthermore, are apt to lead to dehydration of the hydroxyl groups.

For the purpose of shortening the reaction duration, the reaction can be executed at increased pressure, employing pressures up to 50 atmospheres. However, the work can also be carried out under normal pressure, since at this standard pressure the reaction proceeds at a satisfactory rate. The process can be conducted in a batch or continuous manner.

The catalyst introduced can either remain in the end product or it can be hydrolytically split after the completed reaction and neutralized with sodium hydroxide.

The raw products, present after the removal of salts possibly precipitated and of the accumulated water, are practically colorless and do not contain any undesirable by-products. In particular, polyoxyalkylene ethers which usually occur during alkoxylation reactions as by-products are present in the end product of the invention only in inconsequential amounts. The raw products display, moreover, such a degree of reaction of the alcohol used, as it had never before been attained with any of the previous alkoxylation processes and which frequently equals that of a practically complete reaction. Due to this high degree of reaction, the products obtained have a narrow spectrum of alkoxylation homologs, which is of special significance for lower alkoxylated products. These can serve as starting materials for the ether and polyether sulfates which are an important tenside class. It is of importance that, in the sulfating process conducted for the preparation of these ether and polyether sulfates, if at all possible, no hydroxyl groups having various reactivities are present in the starting material. Their presence would be of particular disadvantage, if the difference in the acidities between the starting compound to be reacted and containing hydroxyl groups and the ether or polyether alcohol resulting from the reaction with an alkylene oxide were especially marked as, for example, in the presence of secondary alcohols in addition to their ether and polyether alcohols.

It should be regarded as a startling phenomenon that the tertiary saturated and unsaturated oxonium salts described show such a favorable effect with regard to reaction degree and thus to homologous distribution during the alkoxylation process of alcohols. This is all the more so, as it is known from the literature that cyclic ethers having small rings can be converted with the aid of oxonium salts into long-chain polymers, and that, on the other hand, for example, triethyloxonium fluoborate can effect a decomposition of high molecular weight polyethylene glycol ethers. Moreover, it could not be anticipated that it would be possible by means of the catalyst, to be employed according to the invention, to alkoxylate secondary and, in particular, tertiary alcohols, with the same facility and the corresponding high degree of reaction as the primary alcohols.

The following examples are illustrative of the practice of the invention. They are not, however, to be deemed limitative in any respect.

EXAMPLE 1

The apparatus employed for the experiments consisted of a three-neck flask, which was equipped with stirrer, thermometer, gas inlet and gas outlet devices and thermostatically controlled. Into this flask, 214 gm (1 mol) of n-tetradecanol-1 were introduced and, under an atmosphere of nitrogen, admixed with 0.6 gm (0.3% by weight) of triethyloxonium fluoborate. After the mixture had been heated to the desired temperature of 78° to 83°C. the nitrogen was expelled from the apparatus by being rinsed for 2 minutes with ethylene oxide. Then a stock bottle, containing 132 gm (3.0 mols to 1 mol of alcohol used) of ethylene oxide, was connected to the apparatus, and the ethylene oxide was fed into the said apparatus at a rate which was determined by its being completely taken up in the reaction mixture. The amount of ethylene oxide used was completely absorbed after 1½ hours. The apparatus was rinsed with nitrogen, the catalyst was hydrolytically separated and neutralized with sodium hydroxide. The water accumulated during this operation was distilled in vacuo, and the precipitated salts were removed by filtration. The resultant raw product was practically colorless, and its content of unreacted alcohol was determined by separation by distillation. The content of unreacted alcohol amounted to 5% by weight.

EXAMPLE 2

Sequence and execution of the test were the same as in Example 1. 214 gm (1 mol) of an isomer mixture of secondary n-tetradecanols in the presence of 1.3 gm (0.6% by weight) of triethyloxonium fluoborate were reacted with 422 gm (9.6 mols) of ethylene oxide. The reaction was completed after 2½ hours. Then the reaction mixture was processed as described in Example 1 and gas chromatographically examined, which examination showed no unreacted alcohol to be found.

EXAMPLE 3

The apparatus used for the tests, described in Example 1, was filled with 130 gm of n-octanol-2 (1 mol) and, under an atmosphere of nitrogen, 0.4 gm (0.3% by weight) of trimethyloxonium fluoborate was added. After the nitrogen had been expelled with ethylene oxide and after heating the mixture to a reaction temperature of 139° to 147°C., altogether 88 gm (2.0 mols) of ethylene oxide were introduced. The reaction was completed after 2½ hours. The reaction product obtained was processed as described in Example 1. The resultant end product was nearly colorless. A separation by distillation yielded a 5% content of unreacted alcohol.

EXAMPLE 4

Under an atmosphere of nitrogen, 130 gm (1 mol) of n-octanol-2 were admixed with 0.5 gm (0.4% by weight of triethyloxonium fluoborate in an Ex-protected autoclave. After the autoclave had been purged and rinsed with nitrogen three times, the autoclave was heated to 80°C. Then from a second autoclave, cooled with an ice-sodium chloride mixture, 132 gm (3.0 mols) of ethylene oxide were transferred under pressure into the first autoclave with the aid of nitrogen. The pressures employed ranged between 1.0 and 10 atmospheres. The pressure increase was effected gradually to maintain the temperature of the reaction mixture between 80° and 90°C. The amount of ethylene oxide employed was absorbed within 4 hours. The raw product obtained was processed as described in Example 1. The separation by distillation yielded a content of 1% of unreacted alcohol.

EXAMPLE 5

In the same manner as described in the preceding example, 74 gm (1 mol) of tertiary butanol were reacted with 88 gm (2.0 mols) of ethylene oxide in the presence of 0.33 gm (0.45% by weight) of trimethyloxonium fluoborate. The reaction temperature ranged between 140° and 145°C. The pressures employed ranged between 5.8 and 12.5 atmospheres. The reaction was completed after 3½ hours. After the raw product, processed according to Example 1, was distillatively separated, it still contained 14% of unreacted tertiary butanol.

EXAMPLE 6

In a test sequence and execution corresponding with that of Example 4, 214 gm (1 mol) of a mixture of primary $C_{12}$–$C_{18}$ alkanols were reacted with 92 gm (2.1 mols) of ethylene oxide in the presence of 0.6 gm (0.3% by weight) of triethyloxonium fluoborate. The temperature and pressures employed ranged between 76° and 83°C. and between 1 and 10 atmospheres respectively. The reaction was completed after 3 hours. The column and gas chromatographic examination of the resultant product showed a 10% content of unreacted alcohol.

EXAMPLE 7

In an execution of the test analogous to that in Example 4, 205 gm (1 mol) of a mixture of primary $C_{12}$–$C_{15}$ alkanols, which had been obtained by the oxosynthesis, were reacted with 92 gm (2.1 mols) of ethylene oxide in the presence of 0.6 gm (0.3% by weight) of triethyloxonium fluoborate. The pressures employed ranged between 1 and 10 atmospheres. The test temperature was maintained between 79° and 85°C. The reaction was completed after 1½ hours. The reaction product was processed as described in the preceding examples. The gas chromatographical examination showed an unreacted alcohol content of 6%.

EXAMPLE 8

In a test executed analogously to that in Example 4, 214 gm (1 mol) of a mixture of secondary n-tetradecanols with n-tetradecanol-1 in a ratio of 3 to 1 were reacted with 132 gm (3.0 mols) of ethylene oxide in the presence of 0.6 gm (0.3% by weight) of triethyloxonium fluoborate. The pressures employed ranged between 1 and 11 atmospheres. The reaction temperature ranged between 78° and 83°C. The reaction was completed after 5½ hours. The obtained end product, processed according to the preceding examples, showed an unreacted alcohol content of 13% in the gas chromatographical examination.

EXAMPLE 9

118 gm (1 mol) of hexanediol-1,6 were reacted with 88 gm (2.0 mols) of ethylene oxide in the presence of 0.35 gm of triethyloxonium fluoborate under pressures ranging between 1 and 7 atmospheres and at temperatures between 78° and 84°C., according to Example 4.

The reaction was completed after 3 hours. The raw product processed according to Example 1 had an unreacted alcohol content of 9%.

EXAMPLE 10

In a test sequence corresponding with Example 1, 268 gm of oleyl alcohol (1 mol) were ethoxylated with 88 gm of ethylene oxide at temperatures between 77° and 81°C. under normal pressure in the presence of 0.8 gm (0.3% by weight) of triethyloxonium fluoborate.

of alcohol used, and the ethoxylation was carried out at temperatures between 0° and 50°C in the manner known from the literature. The ethylene oxide amount used again measured 2 mols of ethylene oxide to each mol of alcohol.

After the reactions were completed, the resultant products were gas chromatographically examined with respect to their quantitative composition.

The results obtained are summarized in the following Table I.

TABLE I

| Starting Alcohol | Catalyst | Temp. °C. | Pressure | Unreacted Alcohol % by Weight | | |
|---|---|---|---|---|---|---|
| | | | | Catalyst of Invention | Alkaline Catalyst at 140–150°C | Acid Catalyst at 0°–50°C |
| sec.-n-tetradecanol | Triethyloxonium fluoborate | 76–82 | Normal | 22 | 57 | 32 |
| " | " | 75–80 | 1.0 to 7.5 atm. | 24 | 58 | 33 |
| " | " | 150–161 | Normal | 17 | 60 | 34 |
| n-tetradecanol-1 | " | 75–78 | Normal | 12 | 29 | 17 |
| n-octanol-2 | " | 76–91 | 1.6 to 10 atm. | 9 | 40 | 21 |
| Cyclododecanol | " | 78–94 | 1.0 to 10 atm. | 14 | 46 | 19 |
| n-octanol-2 | Trimethyloxonium fluoborate | 75–80 | Normal | 12 | 55 | 21 |
| " | 1-ethyl-1-oxa-cyclopentanium hexachloroantimonate | 76–82 | Normal | 14 | 55 | 21 |
| " | O-ethyl-camphoroxonium fluoborate | 72–82 | Normal | 11 | 55 | 21 |
| " | 2-ethoxy-1-oxa-cyclopent-1-enium fluoborate | 77–82 | Normal | 9 | 55 | 21 |

The reaction was completed after 1¾ hours. The raw product processed according to Example 1 was colorless and contained 13% of unchanged oleyl alcohol.

EXAMPLE 11

Primary and secondary alcohols were ethoxylated in the presence of saturated and unsaturated tertiary oxonium salts. The tests were conducted in the manner described in the preceding examples under both normal and elevated pressures. Two mols of ethylene oxide were employed to each mol of alcohol. The same alcohols were ethoxylated in the presence of an alkaline catalyst, using again 2 mols of ethylene oxide to each mol of alcohol. For this purpose, the test apparatus, described in Example 4, was filled with the respective alcohol and a 30% sodium methylate-methanol solution. The amount of the sodium methylate solution was measured so that 0.2 to 0.3% by weight of sodium were used, based on the amount of alcohol in the reaction mixture. The methanol was distilled therefrom in vacuo, and the ethoxylation was effected in the usual manner at temperatures between 140° and 150°C. On distillation of the methanol, an equilibrium reaction occurs between the sodium methylate and the alcohol being reacted to give an equilibrim ratio of sodium methylate to sodium alcoholate with most of the catalyst present as the alcoholate of the alcohol being ethoxylated.

In an additional series of tests, the respective alcohols were ethoxylated in the presence of an acid catalyst. It is noted, that acid catalysts are in general of lower interest in technical alkoxylation processes because of their corrosive activity. It seems that $BF_3$ exhibits a lower degree of corrosivity for it has been reported in the literature as a preferred acidic catalyst. $BF_3$ (in the form of $BF_3$-etherate) was added to the alcohol at amounts of 0.2 to 0.3% by weight, based on the amount In another comparison test, 1 mol of an isomeric mixture of secondary n-tetradecanols was reacted in the presence of 0.13% by weight of anhydrous hydrotetrafluoroboric acid (prepared by reacting 1 mol of $BF_3$-etherate with 0.9 mol of anhydrous hydrogen fluoride), with 2 mols of ethylene oxide under normal pressure and at temperatures between 0° and 50°C. The reaction was finished after 4 hours. The end product had a content of 37% of unreacted alcohol.

According to these results, the process of the invention leads in each case to an improved reaction degree, even in relation to the acid catalysts, the employment of which to improve the reaction had already been suggested. This applies in particular to the secondary alkanols having 8 to 24 carbon atoms, ethoxylated in the presence of unsaturated tertiary oxonium salts.

EXAMPLE 12

Comparative examples as in Example II were repeated under the same conditions and catalysts utilizing varying amounts of ethylene oxide per mol of alcohol. After the reactions were completed, the resultant products were examined by gas chromatography with respect to their quantitive composition and their homolog spectra. The results are given in the following tables.

TABLE II

Reaction of 1 mol of n-octanol-2 with 1 mol of ethylene oxide (EO)

| Catalyst | Temp.°C. | Unreacted alcohol % by weight | % ethoxylated compounds with | | |
|---|---|---|---|---|---|
| | | | 1 mol EO | 2 mols EO | 3 mols EO |
| $NaOCH_3$ | 140–150 | 62 | 22 | 14 | 5 |
| $BF_3$ | 0–50 | 38 | 26 | 19 | 10 |

TABLE II-continued

Reaction of 1 mol of n-octanol-2 with 1 mol of ethylene oxide (EO)

| Catalyst | Temp.°C. | Unreacted alcohol % by weight | % ethoxylated compounds with | | |
|---|---|---|---|---|---|
| | | | 1 mol EO | 2 mols EO | 3 mols EO |
| TEOF | 78–85 | 22 | 33 | 22 | 12 |

TABLE III

Reaction of 1 mol of n-octanol-2 with 2 mols of ethylene oxide (EO)

| Catalyst | Temp.°C. | Unreacted alcohol % by weight | % ethoxylated compounds with | | |
|---|---|---|---|---|---|
| | | | 1 mol EO | 2 mols EO | 3 mols EO |
| NaOCH$_3$ | 140–150 | 40 | 10 | 9 | 7 |
| BF$_3$ | 0–50 | 21 | 15 | 18 | 14 |
| TEOF | 76–91 | 9 | 19 | 20 | 16 |

TABLE IV

Reaction of 1 mol of n-octanol-1 with 1 mol of ethylene oxide (EO)

| Catalyst | Temp. °C. | Unreacted alcohol % by weight | % ethoxylated compounds with | | |
|---|---|---|---|---|---|
| | | | 1 mol EO | 2 mols EO | 3 mols EO |
| NaOCH$_3$ | 140–150 | 45 | 22 | 12 | 8 |
| BF$_3$ | 0–50 | 30 | 35 | 20 | 10 |
| TEOF | 76–91 | 22 | 40 | 22 | 9 |

In each instance TEOF represents tetraethyloxonium fluoborate. These tables demonstrate the narrower homolog distribution obtained using the oxonium catalysts in the process of the invention.

EXAMPLE 13

Under an atmosphere of nitrogen, 130 gm (1 mol) of n-octanol-2 were admixed with 0.5 gm (0.4% by weight) of O-ethylcamphoroxonium fluoborate in a three-neck flask equipped with stirrer, thermometer, dropping funnel and reflux condenser, and the reaction apparatus was thermostatically adjusted to 23° to 31°C. 99 gm (1.7 mols) of propylene oxide were slowly added to the mixture through the said dropping funnel. The reaction was finished after 3¼ hours. As described in the preceding examples, the raw product was worked up and separated by distillation. Its content of unreacted n-octanol-2 amounted to 4%.

EXAMPLE 14

The test described in the preceding example was repeated with the difference that instead of propylene oxide, 108 gm (1.5 mols) of butylene oxide were added dropwise to the mixture. The reaction was completed after 3½ hours. A nearly colorless raw product was obtained which contained 14% of unreacted n-octanol-2.

EXAMPLE 15

In a test conducted according to Example 11, 130 gm (1.0 mol) of n-octanol-1 were reacted with 148 gm (2.0 mols) of glycide in the presence of 0.65 gm (0.5% by weight) of 2-ethoxy-1-oxacyclopent-1-enium fluoborate. The reaction temperature ranged between 14° and 37°C. After a reaction period of 3½ hours, a product was obtained which was practically colorless and contained 20% of unreacted alcohol.

EXAMPLE 16

In a test conducted in the same manner as described in Example 11, 130 gm (1 mol) of n-octanol-2 were reacted with 93 gm (1.0 mol) of epichlorhydrin in the presence of 0.5 gm (0.4% by weight) of triethyloxonium fluoborate. The reaction temperature ranged between 75° to 80°C. and the reaction lasted 3 hours. The raw product, which was processed according to the preceding examples, was colorless and showed a content of 11% of unreacted n-octanol-2.

EXAMPLE 17

418 gm (1.72 mols) of an isomeric mixture of secondary $C_{12-19}$ alcohols were admixed in a nitrogen atmosphere with 1.2 gm (0.3% by weight) of triethyloxonium fluoborate in an Ex-protected autoclave. After evacuating the autoclave three times and rinsing with nitrogen, the contents were heated to 80° to 82°C. Then 227 gm (5.16 mols) of ethylene oxide were introduced under pressure. The pressures employed ranged between 0.5 to 6.5 atmospheres gauge. The amount of ethylene oxide used was absorbed within 5 hours. The product contained 9.8% of unreacted starting alcohol. The polyglycol content was about 1.8%. This same secondary alcohol mixture was reacted in the presence of 0.2% by weight of borontrifluoride (in the form of its diethyletherate) with ethylene oxide in a molar ratio of 1:3 at 79°C. The reaction product contained 15.6% of unreacted starting alcohols and 2.5% of polyglycols.

EXAMPLE 18

214 gm (1 mol) of sec.-tetradecanol (isomeric mixture) were placed in a three-necked flask, which was provided with a stirrer, thermometer, gas-inlet frit and gas outlet device and a thermostat to control the temperature, and were mixed with 0.6 gm (0.3% by weight) of diethoxycarbonium fluoborate in an atmosphere of nitrogen. The mixture was heated to 72° to 80°C. and a total of 88 gm (2 mols) of ethylene oxide was added at this temperature. The amount of ethylene oxide added was absorbed after 2 hours. The catalyst was then hydrolytically decomposed and the reaction mixture was neutralized with caustic soda solution. The water introduced during this reaction was distilled off in vacuo and precipitated salt was filtered off. The crude product so obtained was practically colorless. Its content of unreacted alcohol, which was found upon separation by distillation, was 26% by weight.

When the same alcohol is reacted with 2 mols of ethylene oxide in the usual way at 140° to 150°C in the presence of a basic catalyst (0.2 to 0.3% by weight of sodium, inserted in the form of sodium methylate), the reaction product still contains 57% by weight of unreacted alcohol. When 2 mols of ethylene oxide are added on to the same alcohol in the presence of an acid catalyst (0.2 to 0.3% by weight of boron trifluoride, based on the amount of alcohol) at temperatures between 0° and 50°C., a product with a content of 32% by weight of residual alcohol results.

EXAMPLE 19

In the same way as in Example 18 214 gm (1 mol) of n-tetradecanol-1 were reacted with 88 gm (2 mols) of ethylene oxide at 75° to 78°C. in the presence of 0.6 gm (0.3% by weight) of diethoxycarbonium fluoborate. The reaction product still contained 12% by weight of unreacted alcohol. The addition of 2 mols of ethylene oxide to the same alcohol, when catalyzed by basic or acid catalysts as in Example 18, provided reaction products with residual alcohol contents of 29 and 17% by weight, respectively.

EXAMPLE 20

Example 18 was repeated with the exception that 0.6 gm (0.3% by weight) of 1:1 mixture of diethoxycarbonium fluoborate and triethyloxonium fluoborate was used as catalyst. The reaction was finished after one hour. A reaction product with a residual alcohol content of 24% by weight resulted.

The advantages obtained by the process of the invention consist essentially in that, with the catalyst to be employed according to the invention, a high reaction degree of the alcohol and, in relation thereto, a narrow spectrum of alkoxylation homologs of the adducts can be obtained. Therefore, the ether and polyether adducts are available in greater yields in the reaction mixture and the reaction mixture can be used as a raw product, that is to say, without separation from the unreacted starting material or without additional processing. This applies in particular to the alkylene oxide adducts of the secondary and tertiary alcohols which, according to the methods previously employed, could not be alkoxylated to a satisfactory degree.

Additional advantages of the process of the invention are the possibility of working at relatively low temperatures, which results in an improvement of color and greater purity of the products, as well as the possibility of working under normal pressure which allows a decrease in the expenditures concerning the apparatus used.

The preceding specific embodiments are illustrative of the practice of the invention. It is to be understood, however, that other expedients, either explained above or known in the art, can be employed without departing from the spirit of the invention.

We claim:

1. A process for alkoxylation of compounds containing an alcoholic hydroxyl group which compises reacting a secondary alkanol having from 8 to 15 carbon atoms with an epoxide of the formula

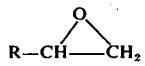

wherein R is a member selected from the group consisting of hydrogen, alkyl having 1 to 2 carbon atoms, hydroxyalkyl having 1 to 2 carbon atoms and haloalkyl having 1 to 2 carbon atoms, under alkoxylation conditions at temperatures between 0° and 200°C in the presence of from 0.05 % to 5% by weight, based on the weight of said compound containing hydroxyl groups, of a tertiary oxonium salt of the formula

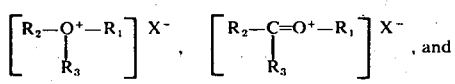, and

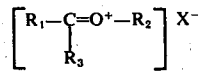

wherein X represents a halogeno-complex anion selected from the group consisting of $BF_4^-$, $FeCl_4^-$, $AlCl_4^-$, $SbCl_6^-$ and $SnCl_6^=$; $R_1$ represents a member selected from the group consisting of alkyl having from 1 to 4 carbon atoms, alkoxy having from 1 to 4 carbon atoms, haloalkyl having from 1 to 4 carbon atoms and phenyl; $R_2$ and $R_3$ are members selected from the group consisting of alkyl having 1 to 24 carbon atoms, alkoxy having from 1 to 4 carbon atoms, haloalkyl having 1 to 4 carbon atoms, phenyl, phenylvinyl and when taken together, alkylene having 3 to 14 carbon atoms, oxaalkylene having 2 to 13 carbon atoms, thiaalkylene having 2 to 13 carbon atoms, azaalkylene having 2 to 13 carbon atoms, alkenylene having 3 to 14 carbon atoms, alkadienylene having 4 to 14 carbon atoms and benzobutadienylene; and recovering said alkoxylated compounds.

2. A process for alkoxylation of compound containing an alcoholic hydroxyl group which comprises reacting a secondary alkanol having from 8 to 15 carbon atoms with an epoxide of the formula

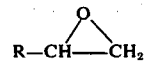

wherein R is a member selected from the group consisting of hydrogen, alkyl having 1 to 2 carbon atoms, hydroxyalkyl having 1 to 2 carbon atoms and haloalkyl having 1 to 2 carbon atoms, under alkoxylation conditions at temperatures between 0° and 200° in the presence of from 0.05 to 5% by weight, based on the weight of said compound containing hydroxyl groups, of a tertiary oxonium salt of the formula

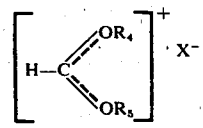

wherein X represents a halogeno-complex anion selected from the group consisting of $BF_4^-$, $FeCl_4^-$, $AlCl_4^-$, $SbCl_6^-$ and $SnCl_6^=$; $R_4$ and $R_5$ are members selected from the group consisting of alkyl having 1 to 24 carbon atoms, haloalkyl having 1 to 8 carbon atoms, phenyalkyl having from 7 to 10 carbon atoms, alkoxyalkyl having from 2 to 24 carbon atoms and cycloalkylalkyl having from 6 to 10 carbon atoms; and recovering said alkoxylated compounds.

3. A process for alkoxylation of compounds containing an alcoholic hydroxyl group which comprises reacting an isomeric mixture of secondary n-tetradecanols with an epoxide of the formula

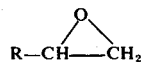

wherein R is a member selected from the group consisting of hydrogen, alkyl having 1 to 2 carbon atoms, hydroxyalkyl having 1 to 2 carbon atoms and haloalkyl having 1 to 2 carbon atoms, under alkoxylation conditions at temperatures between 0° and 200°C in the presence of from 0.05 to 5% by weight, based on the weight of said compound containing hydroxyl groups, of a tertiary oxonium salt of the formula selected from the group consisting of

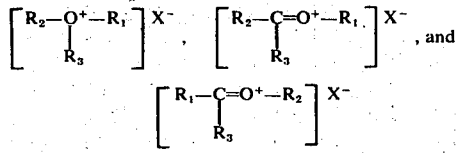, and

wherein X represents a halogeno-complex anion selected from the group consisting of $BF_4^-$, $FeCl_4^-$, $AlCl_4^-$, $SbCl_6^-$ and $SnCl_6^=$; $R_1$ represents a member selected from the group consisting of alkyl having from 1 to 4 carbon atoms, alkoxy having from 1 to 4 carbon atoms, haloalkyl having from 1 to 4 carbon atoms and phenyl; $R_2$ and $R_3$ are members selected from the group consisting of alkyl having 1 to 24 carbon atoms, alkoxy having 1 to 4 carbon atoms, haloalkyl having 1 to 4 carbon atoms, phenyl, phenylvinyl and, when taken together, alkylene having 3 to 14 carbon atoms, oxaalkylene having 2 to 13 carbon atoms, thiaalkylene having 2 to 13 carbon atoms, azaalkylene having 2 to 13 carbon atoms, alkenylene having 3 to 14 carbon atoms, alkadienylene having 4 to 14 carbon atoms and benzobutadienylene; and recovering said alkoxylated compounds.

4. A process for alkoxylation of compounds containing an alcoholic hydroxyl group which comprises reacting a fatty alcohol mixture containing from 8 to 24 carbon atoms as obtained by hydrogenation of fatty acid mixtures with an epoxide of the formula

wherein R is a member selected from the group consisting of hydrogen, alkyl having 1 to 2 carbon atoms, hydroxyalkyl having 1 to 2 carbon atoms and haloalkyl having 1 to 2 carbon atoms, under alkoxylation conditions at temperatures between 0° and 200°C in the presence of from 0.05 to 5% by weight, based on the weight of said compound containing hydroxyl groups, of a tertiary oxonium salt of the formula

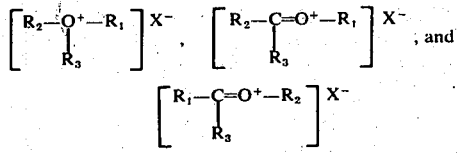, and

wherein X represents a halogeno-complex anion selected from the group consisting of $BF_4^-$, $FeCl_4^-$, $AlCl_4^-$, $SbCl_6^-$ and $SnCl_6^=$; $R_1$ represents a member selected from the group consisting of alkyl having from 1 to 4 carbon atoms, alkoxy having from 1 to 4 carbon atoms, haloalkyl having from 1 to 4 carbon atoms and phenyl; $R_2$ and $R_3$ are members selected from the group consisting of alkyl having 1 to 24 carbon atoms, alkoxy having 1 to 4 carbon atoms, haloalkyl having 1 to 4 carbon atoms, phenyl, phenylvinyl and, when taken together, alkylene having 3 to 14 carbon atoms, oxaalkylene having 2 to 13 carbon atoms, thiaalkylene having 2 to 13 carbon atoms, azaalkylene having 2 to 13 carbon atoms, alkenylene having 3 to 14 carbon atoms, alkadienylene having 4 to 14 carbon atoms and benzobutadienylene; and recovering said alkoxylated compounds.

5. The process of claim 4 wherein said reaction mixture is maintained at atmospheric pressure.

6. The process of claim 4 wherein said reaction mixture is maintained at elevated pressures up to 50 atmospheres.

7. The process of claim 4 wherein said tertiary oxonium salt has the formula

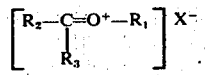

8. The process of claim 4 wherein said tertiary oxonium salt has the formula

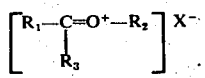

9. The process of claim 4 wherein said tertiary oxonium salt is present in an amount of from 0.1 to 1.5% by weight, based on the weight of said compound containing hydroxyl groups.

10. The process of claim 4 wherein said tertiary oxonium salt has the formula

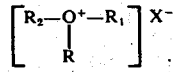

11. A process for alkoxylation of compounds containing an alcoholic hydroxyl group which comprises reacting an isomer mixture of secondary n-tetradecanols with an epoxide of the formula

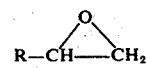

wherein R is a member selected from the group consisting of hydrogen, alkyl having 1 to 2 carbon atoms, hydroxyalkyl having 1 to 2 carbon atoms and haloalkyl having 1 to 2 carbon atoms, under alkoxylation conditions at temperatures between 0° and 200°C in the presence of from 0.05 to 5% by weight, based on the weight of said compound containing hydroxyl groups, of a tertiary oxonium salt of the formula

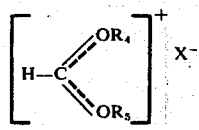

wherein X represents a halogeno-compound anion selected from the group consisting of $BF_4^-$, $FeCl_4^-$, $AlCl_4^-$, $SbCl_6^-$ and $SnCl_6^=$; $R_4$ and $R_5$ are members selected from the group consisting of alkyl having 1 to 24 carbon atoms, haloalkyl having 1 to 8 carbon atoms, phenylalkyl having from 7 to 10 carbon atoms, alkoxyalkyl having from 2 to 24 carbon atoms and cycloalkylalkyl having from 6 to 10 carbon atoms; and recovering said alkoxylated compounds.

12. A process for alkoxylation of compounds containing an alcoholic hydroxyl group which comprises reacting a fatty alcohol mixture containing from 8 to 24 carbon atoms as obtained by hydrogenation of fatty acid mixtures with an epoxide of the formula

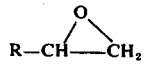

wherein R is a member selected from the group consisting of hydrogen, alkyl having 1 to 2 carbon atoms, hydroxyalkyl having 1 to 2 carbon atoms and haloalkyl having 1 to 2 carbon atoms, under alkoxylation conditions at temperatures between 0° and 200°C in the presence of from 0.05 to 5% by weight, based on the weight of said compound containing hydroxyl groups, of a tertiary oxonium salt of the formula

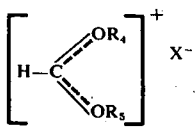

wherein X represents a halogeno-complex anion selected from the group consisting of $BF_4^-$, $FeCl_4^-$, $AlCl_4^-$, $SbCl_6^-$ and $SnCl_6^=$; $R_4$ and $R_5$ are members selected from the group consisting of alkyl having 1 to 24 carbon atoms, haloalkyl having 1 to 8 carbon atoms, phenylalkyl having from 7 to 10 carbon atoms, alkoxyalkyl having from 2 to 24 carbon atoms and cycloalkylalkyl having from 6 to 10 carbon atoms; and recovering said alkoxylated compounds.

13. The process of claim 12 wherein $R_4$ and $R_5$ are alkyl having from 1 to 5 carbon atoms.

14. The process of claim 12 wherein said reaction mixture is maintained at atmospheric pressure.

15. The process of claim 12 wherein said reaction mixture is maintained at elevated pressures up to 50 atmospheres.

16. The process of claim 12 wherein said tertiary oxonium salt is present in an amount of from 0.1 to 1.5% by weight, based on the weight of said compound containing hydroxyl groups.

* * * * *